United States Patent
Fuseya et al.

(10) Patent No.: US 11,883,067 B2
(45) Date of Patent: Jan. 30, 2024

(54) DILATOR

(71) Applicant: ASAHI INTECC CO., LTD., Seto (JP)

(72) Inventors: Yukihiro Fuseya, Seto (JP); Marina Tsuzuku, Seto (JP); Daisuke Kurita, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 304 days.

(21) Appl. No.: 17/205,952

(22) Filed: Mar. 18, 2021

(65) Prior Publication Data
US 2021/0204975 A1    Jul. 8, 2021

Related U.S. Application Data

(63) Continuation of application No. PCT/JP2018/035093, filed on Sep. 21, 2018.

(51) Int. Cl.
*A61B 17/34*    (2006.01)
*A61B 1/00*    (2006.01)

(52) U.S. Cl.
CPC ............ *A61B 17/3423* (2013.01); *A61B 1/00* (2013.01); *A61B 2017/3425* (2013.01); *A61B 2017/3458* (2013.01)

(58) Field of Classification Search
CPC ........ A61B 17/3423; A61B 2017/3425; A61B 2017/3458; A61B 1/00135
See application file for complete search history.

(56) References Cited

U.S. PATENT DOCUMENTS

| | | | |
|---|---|---|---|
| 4,491,126 A | 1/1985 | Cullor | |
| 4,629,450 A | 12/1986 | Suzuki et al. | |
| 5,279,567 A * | 1/1994 | Ciaglia | A61B 17/3415 604/117 |
| 5,403,336 A | 4/1995 | Kieturakis et al. | |
| 2001/0047175 A1 | 11/2001 | Doubler et al. | |
| 2002/0077655 A1 | 6/2002 | Frova | |
| 2004/0184897 A1 * | 9/2004 | Levey | F16B 39/30 411/411 |

(Continued)

FOREIGN PATENT DOCUMENTS

| | | | |
|---|---|---|---|
| EP | 0 542 103 A1 | 5/1993 | |
| EP | 1 731 105 A1 | 12/2006 | |

(Continued)

*Primary Examiner* — Nicholas W Woodall
(74) *Attorney, Agent, or Firm* — Oliff PLC

(57) ABSTRACT

A dilator that includes a hollow shaft including a tapered section having a diameter increasing from a distal end toward a proximal end, and a spirally-arranged protruding portion provided on an outer peripheral surface of the hollow shaft and including spirally-arranged protruding sections and gaps between adjacent spirally-arranged protruding sections along an axial direction of the hollow shaft. The spirally-arranged protruding portion includes an apex section having the greatest height from the outer peripheral surface in a transverse cross-section thereof, and a side surface section facing outward and extending from the apex section toward the outer peripheral surface. The side surface section includes an inclined surface inclined substantially linearly toward at least one of the distal and proximal end direction between the outer peripheral surface and the apex section in the transverse cross-section of the spirally-arranged protruding portion.

3 Claims, 13 Drawing Sheets

(56) References Cited

U.S. PATENT DOCUMENTS

| | | |
|---|---|---|
| 2007/0088230 A1 | 4/2007 | Terashi et al. |
| 2011/0092909 A1* | 4/2011 | Andersson ............. A61B 17/02 604/164.04 |
| 2012/0029281 A1 | 2/2012 | Frassica et al. |
| 2012/0149985 A1 | 6/2012 | Frassica et al. |
| 2013/0274782 A1* | 10/2013 | Morgan ........... A61B 17/00234 606/185 |
| 2014/0046357 A1 | 2/2014 | Neoh |
| 2015/0073429 A1* | 3/2015 | Sartor ................ A61B 17/0218 606/110 |
| 2015/0164552 A1* | 6/2015 | Chen ...................... A61B 90/00 600/204 |
| 2017/0202575 A1 | 7/2017 | Stanfield et al. |

FOREIGN PATENT DOCUMENTS

| | | |
|---|---|---|
| EP | 3804642 A1 | 4/2021 |
| JP | S60-234671 A | 11/1985 |
| JP | 2002-177289 A | 6/2002 |
| JP | 2007-098120 A | 4/2007 |
| JP | 5448200 B2 | 3/2014 |
| JP | 2014-524807 A | 9/2014 |
| JP | 5582612 B2 | 9/2014 |
| JP | 2017-523019 A | 8/2017 |
| WO | 2006/071785 A2 | 7/2006 |
| WO | 2013/038720 A1 | 3/2013 |
| WO | 2018-180209 A1 | 10/2018 |

* cited by examiner

[FIG.1]
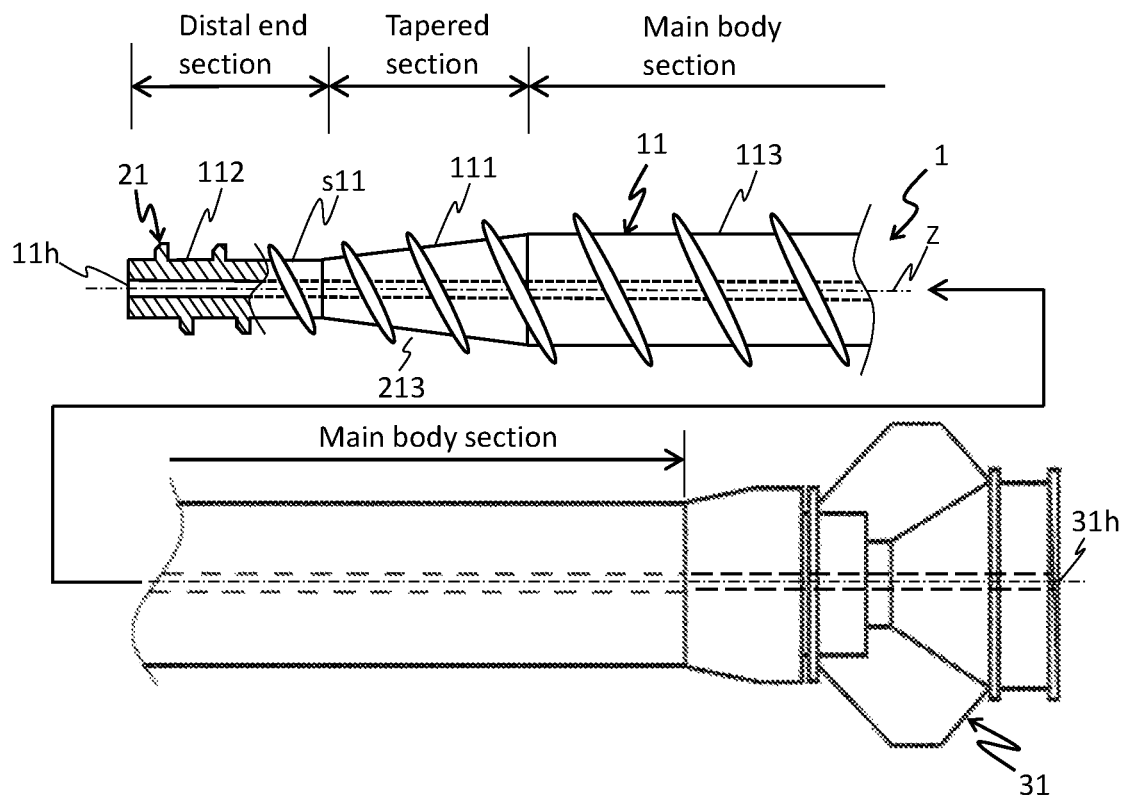
[FIG.2]
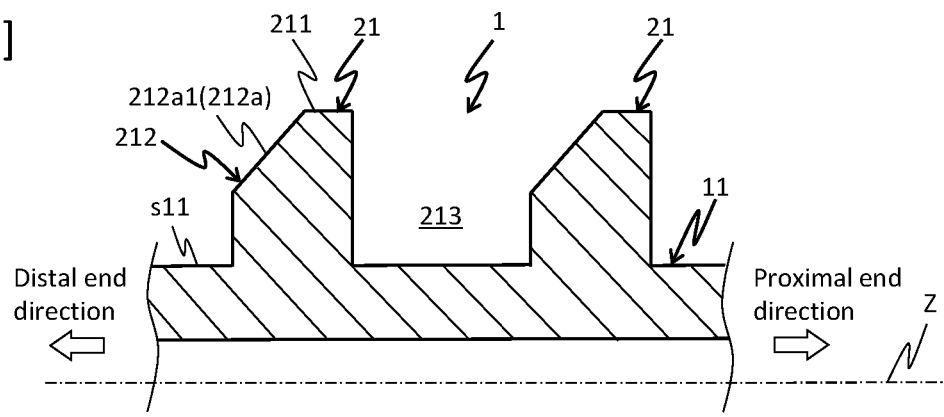

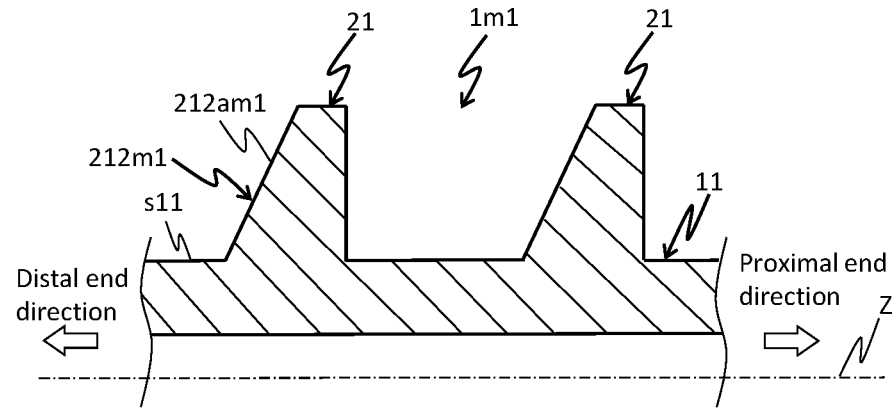
[FIG.3A]
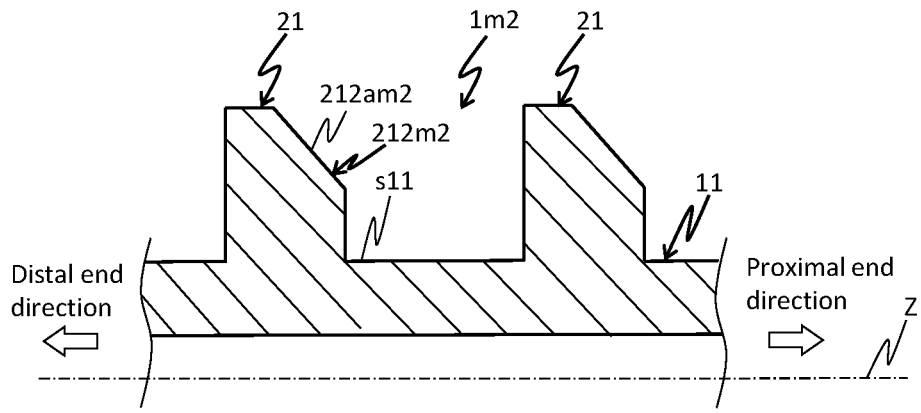
[FIG.3B]
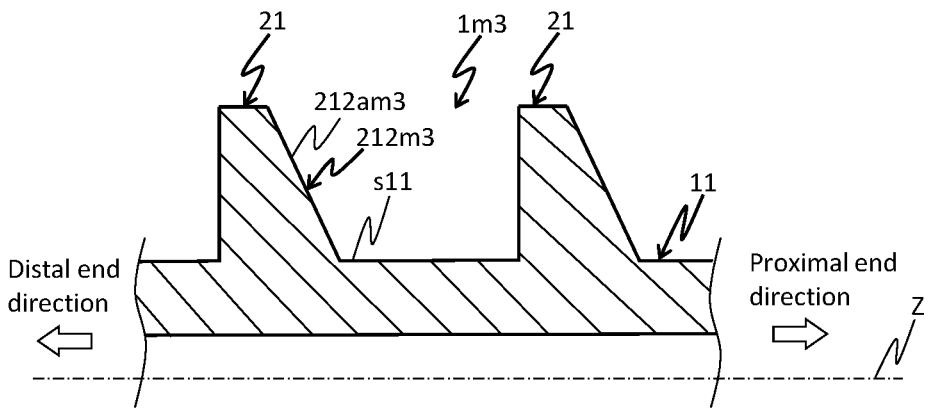
[FIG.3C]

[FIG.3D]
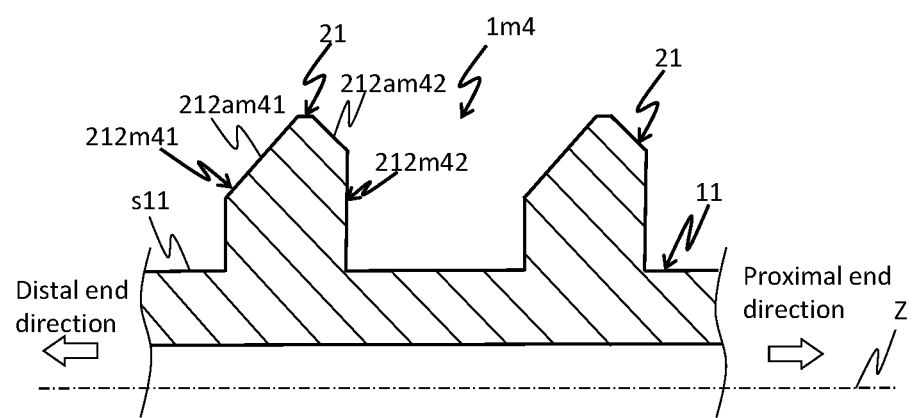
[FIG.3E]
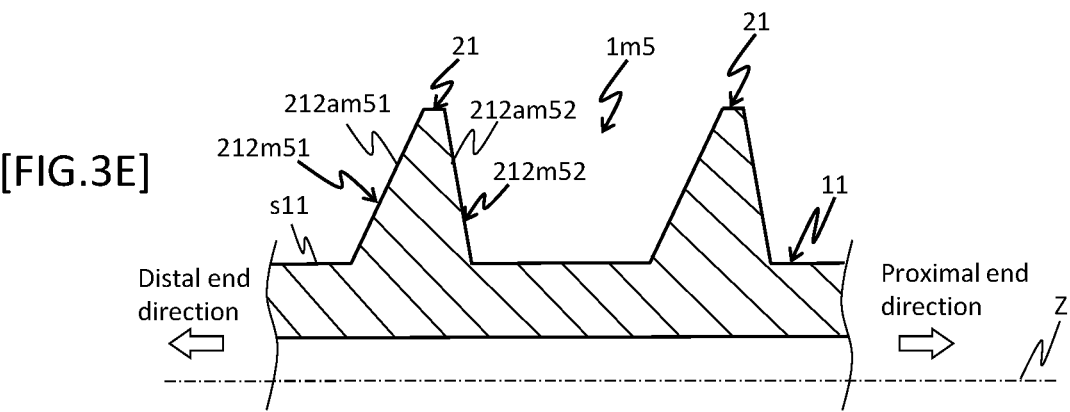

[FIG.4]
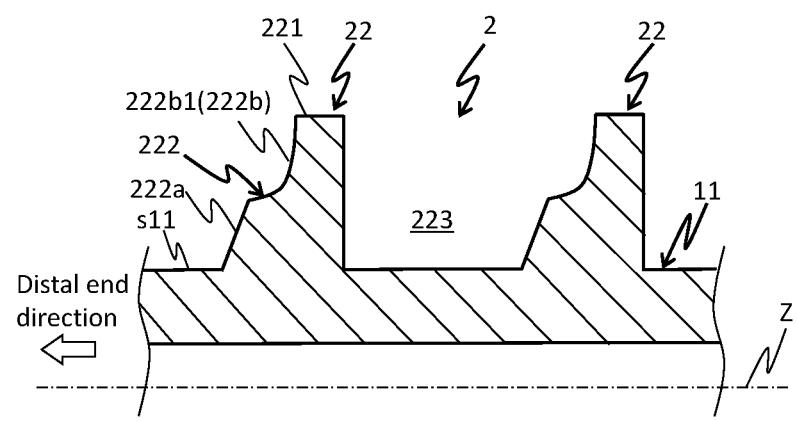

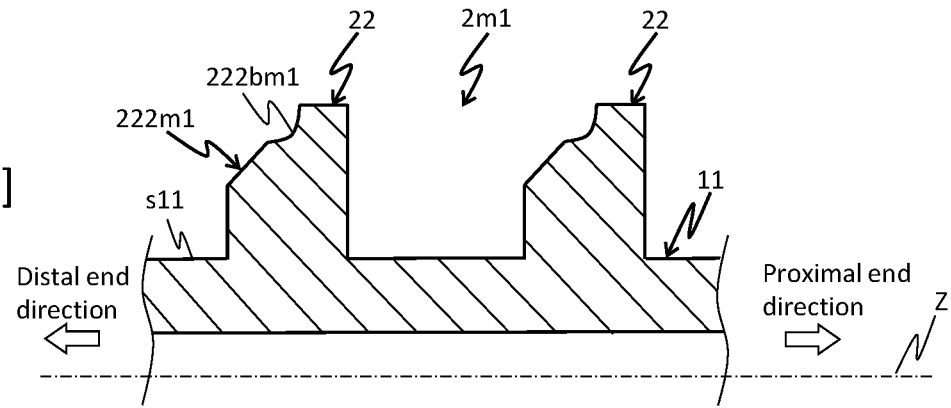
[FIG.5A]
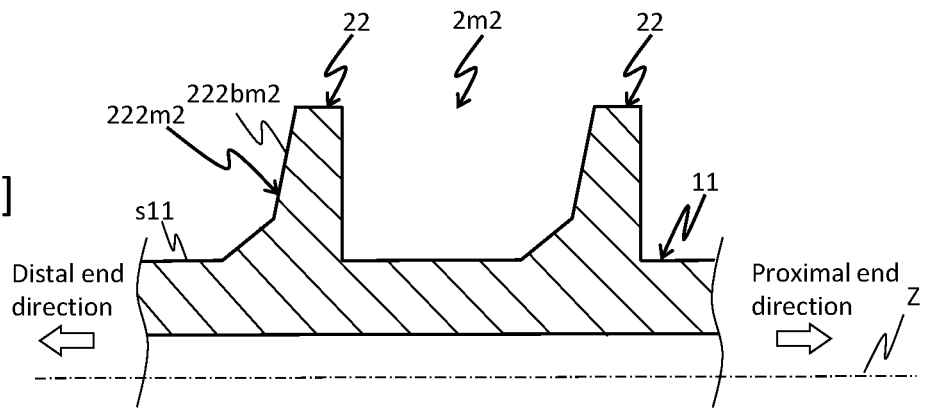
[FIG.5B]
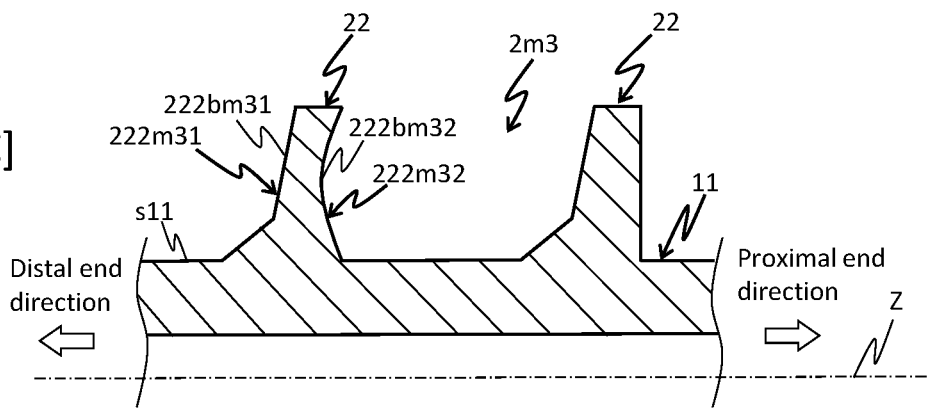
[FIG.5C]

[FIG.6]
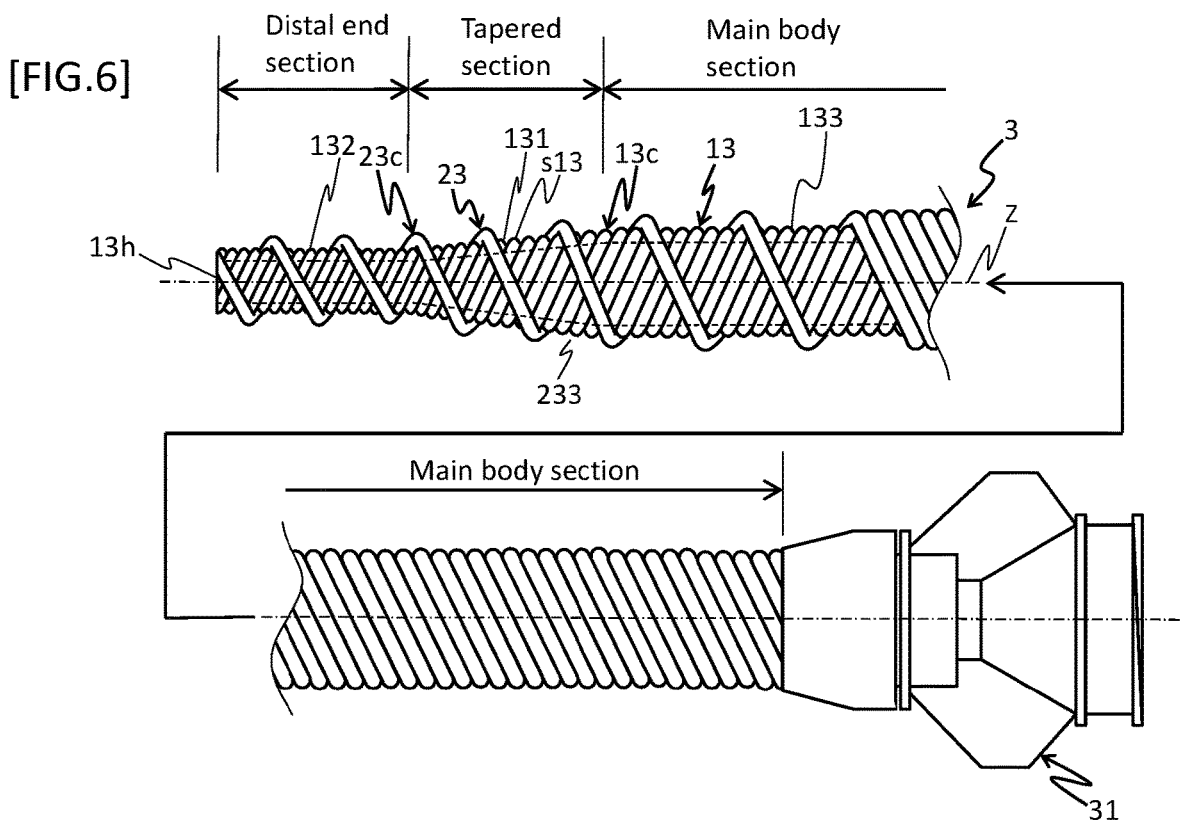
[FIG.7]
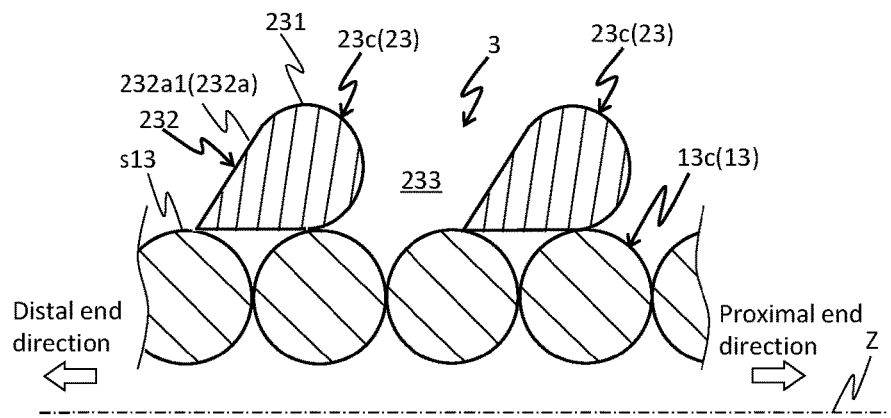

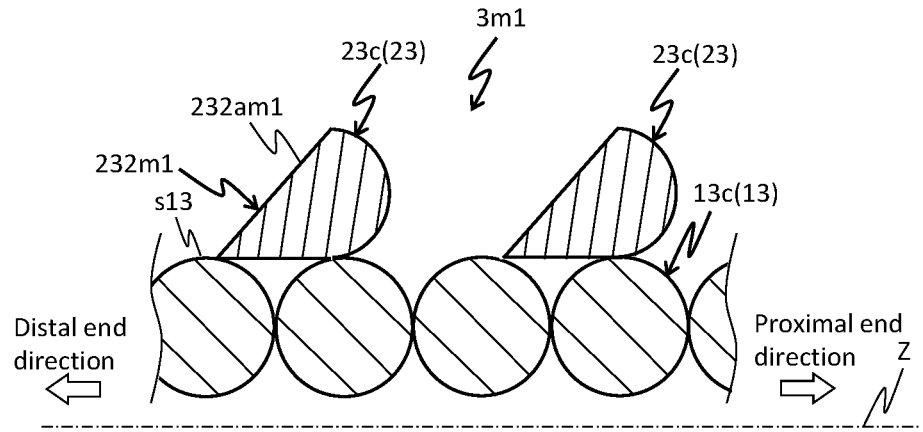
[FIG.8A]
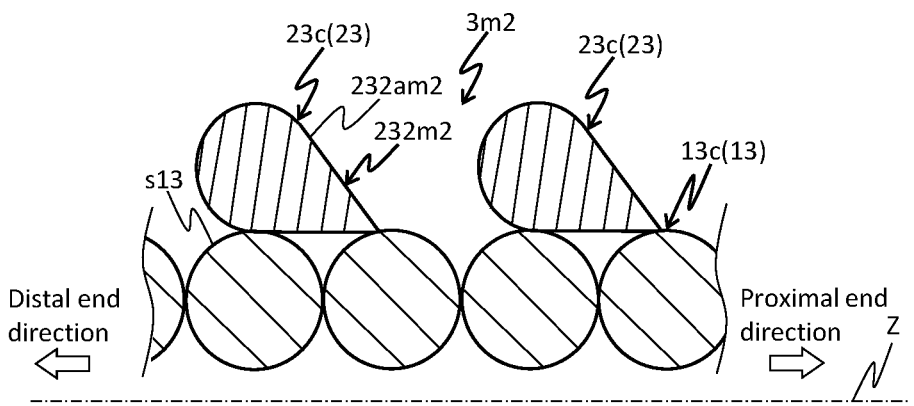
[FIG.8B]
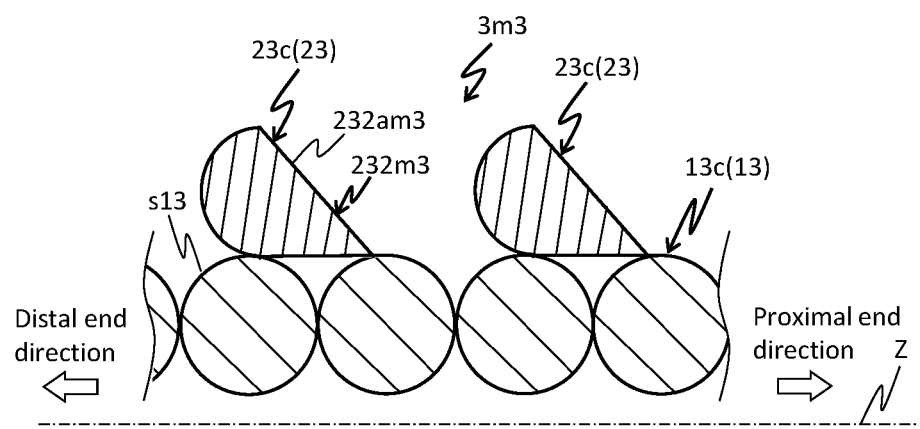
[FIG.8C]

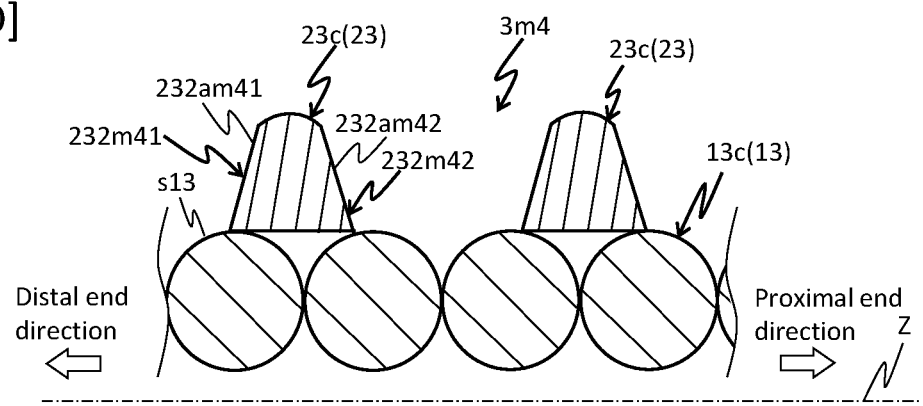
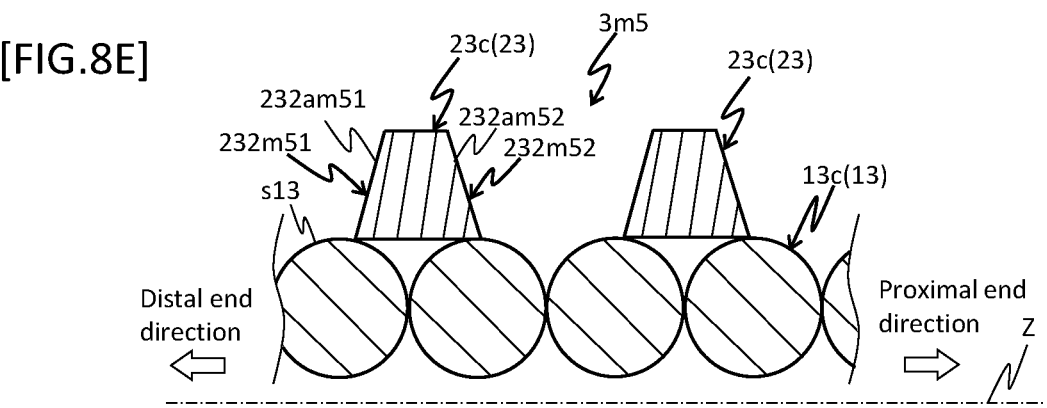

[FIG.9]
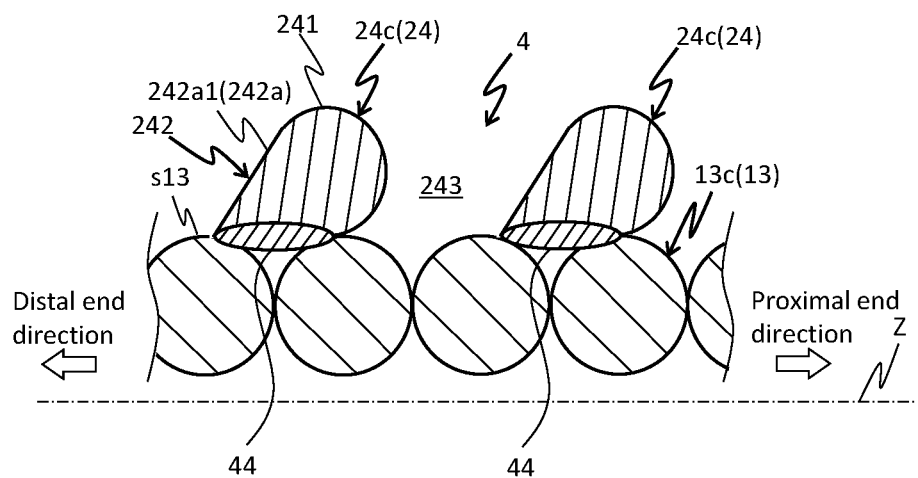

[FIG.10]
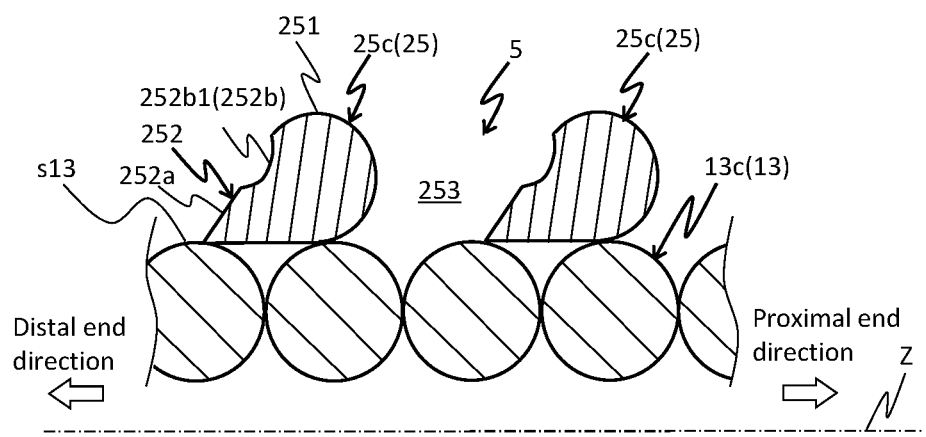

[FIG.11A]
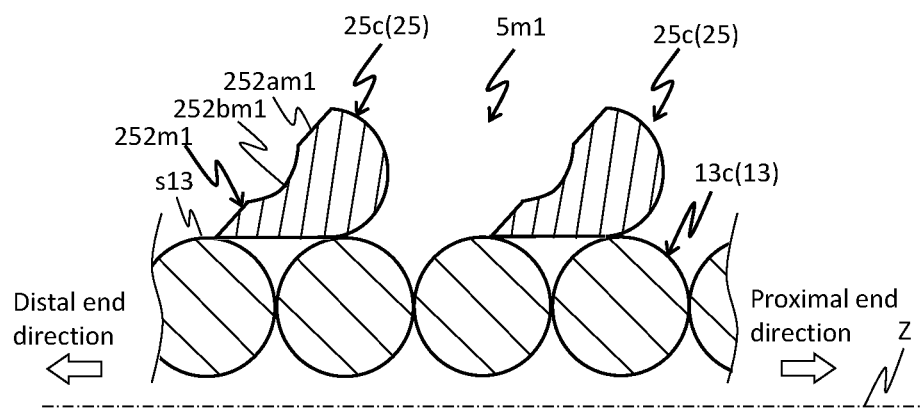
[FIG.11B]
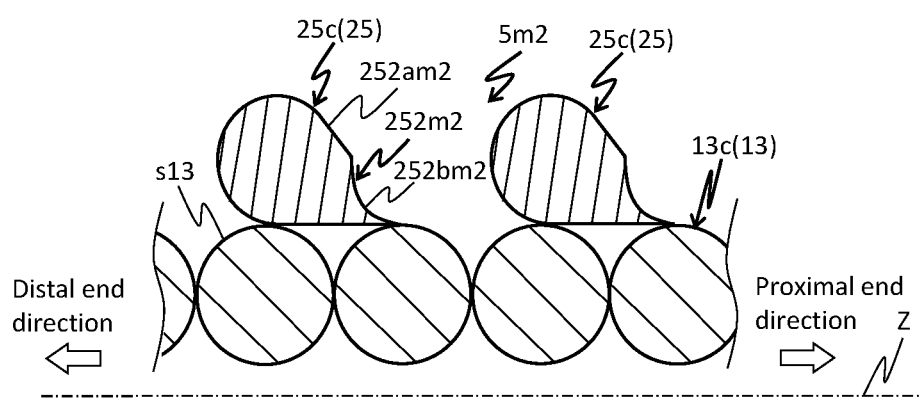
[FIG.11C]
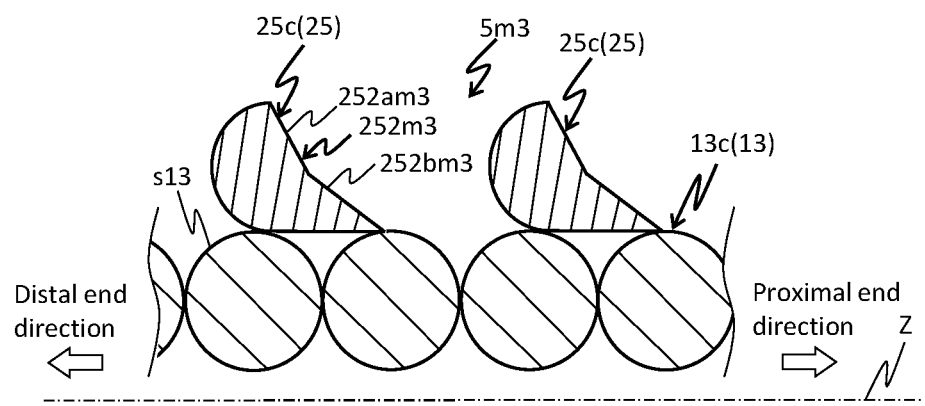
[FIG.11D]
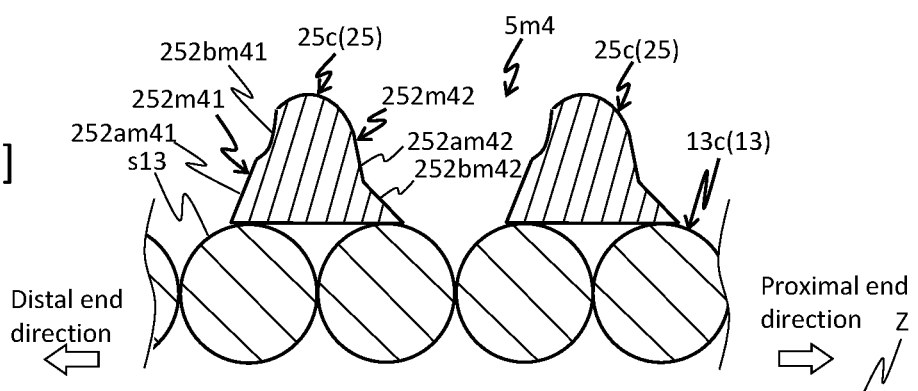

[FIG.12]
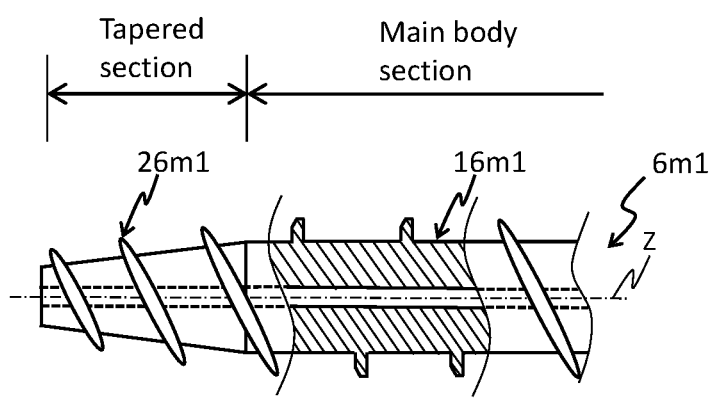
[FIG.13]
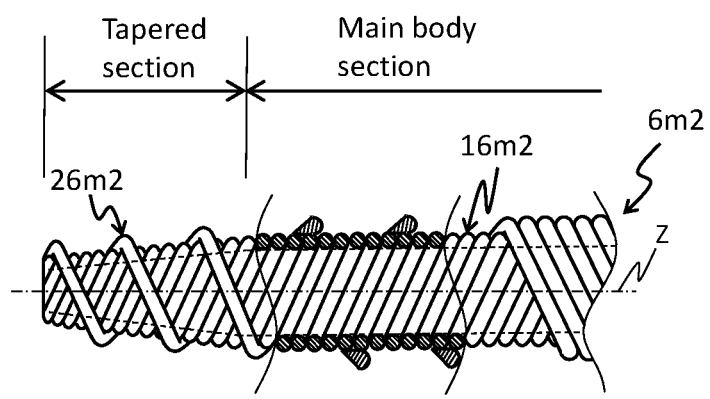

[FIG.14]
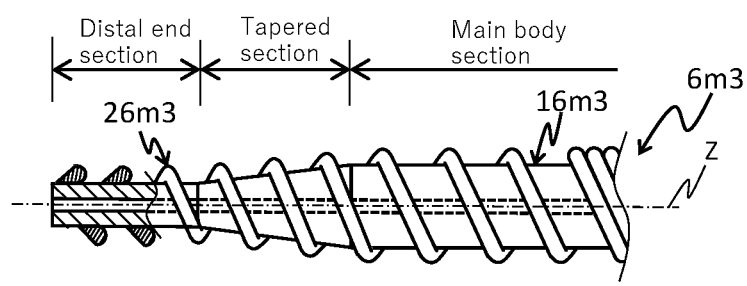
[FIG.15]
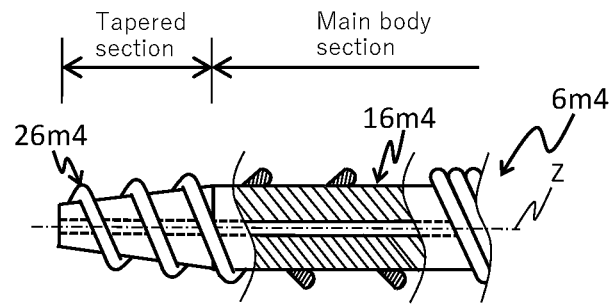

DILATOR

CROSS REFERENCE TO RELATED APPLICATION

This application is a continuation application of International Application No. PCT/JP2018/035093, filed Sep. 21, 2018. The contents of this application are incorporated herein by reference in their entirety.

BACKGROUND

This application relates to a dilator.

A known example of a device for dilating a hole formed in a wall of an organ such as a stomach and a liver or a constricted part in a body cavity such as a bile duct and a pancreatic duct includes a dilator in which a wire is wound around an outer periphery of a shaft including a tapered section to form a helical screw, as discussed in Japanese Patent Document JP 2014-524807.

According to such a dilator, after a distal end of the shaft is inserted into a hole or the like, the shaft is rotated to be advanced by a screwing action of the helical screw, or the shaft is linearly pushed forward to be advanced, and thus, the hole is dilated by the tapered section.

However, in a dilator in which a helical screw is formed by winding a wire as described above, when the shaft is linearly pushed in or pulled out, the wire hits a contact object and the resistance exerted on a hollow shaft increases, so that it may not be possible to smoothly advance and retreat the dilator.

SUMMARY

The disclosed embodiments have been made in accordance with the above circumstances, and an object thereof is to provide a dilator that includes a spirally-arranged protruding portion and is capable of advancing and/or retreating by a rotation of a hollow shaft, and is also capable of smoothly performing a movement when being pushed in and/or pulled out linearly.

To achieve the above object, a dilator according to an embodiment of the present disclosure includes: a dilator including a hollow shaft including a tapered section having a diameter increasing from a distal end toward a proximal end, and a spirally-arranged protruding portion being provided on an outer peripheral surface of the hollow shaft and including gaps between neighboring sections of the spirally-arranged protruding portion along an axial direction of the hollow shaft, in which:

(1) the spirally-arranged protruding portion includes an apex section having a greatest height from the outer peripheral surface in a transverse cross-section of the spirally-arranged protruding portion, (2) a side surface section facing outward and extending from the apex section toward the outer peripheral surface, and (3) the side surface section includes an inclined surface inclined substantially linearly toward a distal end direction and/or a proximal end direction between the outer peripheral surface and the apex section in the transverse cross-section of the spirally-arranged protruding portion.

It is noted that, in the present specification, the "distal end direction" refers to a direction along the axial direction of the hollow shaft and a direction in which the tapered section is located with respect to the main body section. Further, the "proximal end direction" refers to a direction along the axial direction of the dilator and a direction opposite to the distal end direction. Further, the "distal end" refers to an end section of any member or portion in the distal end direction, and the "proximal end" refers to an end section of any member or portion in the proximal end direction, respectively.

BRIEF DESCRIPTION OF THE DRAWINGS

FIG. 1 is a schematic side view entirely illustrating a dilator of the disclosed embodiments;

FIG. 2 is an enlarged schematic end view illustrating a spirally-arranged protruding portion of FIG. 1;

FIG. 3A is a schematic end view illustrating a dilator of the disclosed embodiments in which the spirally-arranged protruding portion is enlarged;

FIG. 3B is a schematic end view illustrating a dilator of the disclosed embodiments in which the spirally-arranged protruding portion is enlarged;

FIG. 3C is a schematic end view illustrating a dilator of the disclosed embodiments in which the spirally-arranged protruding portion is enlarged;

FIG. 3D is a schematic end view illustrating a dilator of the disclosed embodiments in which the spirally-arranged protruding portion is enlarged;

FIG. 3E is a schematic end view illustrating a dilator of the disclosed embodiments in which the spirally-arranged protruding portion is enlarged;

FIG. 4 is an enlarged schematic end view illustrating a spirally-arranged protruding portion of a dilator of the disclosed embodiments;

FIG. 5A is a schematic end view illustrating a dilator of the disclosed embodiments in which the spirally-arranged protruding portion is enlarged;

FIG. 5B is a schematic end view illustrating a dilator of the disclosed embodiments in which the spirally-arranged protruding portion is enlarged;

FIG. 5C is a schematic end view illustrating a dilator of the disclosed embodiments in which the spirally-arranged protruding portion is enlarged;

FIG. 6 is a schematic side view entirely illustrating a dilator of the disclosed embodiments;

FIG. 7 is an enlarged schematic end view illustrating a spirally-arranged protruding portion of FIG. 6;

FIG. 8A is a schematic end view illustrating a dilator of the disclosed embodiments in which the spirally-arranged protruding portion is enlarged;

FIG. 8B is a schematic end view illustrating a dilator of the disclosed embodiments in which the spirally-arranged protruding portion is enlarged;

FIG. 8C is a schematic end view illustrating a dilator of the disclosed embodiments in which the spirally-arranged protruding portion is enlarged;

FIG. 8D is a schematic end view illustrating a dilator of the disclosed embodiments in which the spirally-arranged protruding portion is enlarged;

FIG. 8E is a schematic end view illustrating a dilator of the disclosed embodiments in which the spirally-arranged protruding portion is enlarged;

FIG. 9 is an enlarged schematic end view illustrating a spirally-arranged protruding portion of a dilator of the disclosed embodiments;

FIG. 10 is an enlarged schematic end view illustrating a spirally-arranged protruding portion of a dilator of the disclosed embodiments;

FIG. 11A is a schematic end view illustrating a dilator of the disclosed embodiments in which the spirally-arranged protruding portion is enlarged;

FIG. 11B is a schematic end view illustrating a dilator of the disclosed embodiments in which the spirally-arranged protruding portion is enlarged;

FIG. 11C is a schematic end view illustrating a dilator of the disclosed embodiments in which the spirally-arranged protruding portion is enlarged;

FIG. 11D is a schematic end view illustrating a dilator of the disclosed embodiments in which the spirally-arranged protruding portion is enlarged;

FIG. 12 is a partially cut schematic side view illustrating a part of a dilator of the disclosed embodiments;

FIG. 13 is a partially cut schematic side view illustrating a part of a dilator of the disclosed embodiments;

FIG. 14 is a partially cut schematic side view illustrating a part of a dilator of the disclosed embodiments; and FIG. 15 is a partially cut schematic side view illustrating a part of a dilator of the disclosed embodiments.

DETAILED DESCRIPTION

In the disclosed embodiments, the dilator includes a hollow shaft including a tapered section having a diameter increasing from a distal end toward a proximal end, and a spirally-arranged protruding portion being provided on an outer peripheral surface of the hollow shaft and including gaps between neighboring sections of the spirally-arranged protruding portion along an axial direction of the hollow shaft. The spirally-arranged protruding portion includes an apex section having a greatest height from the outer peripheral surface in a transverse cross-section of the spirally-arranged protruding portion, and a side surface section facing outward and extending from the apex section toward the outer peripheral surface. The side surface section includes an inclined surface inclined substantially linearly toward a distal end direction and/or a proximal end direction of the hollow shaft between the outer peripheral surface and the apex section in the transverse cross-section of the spirally-arranged protruding portion.

Some embodiments will be described below with reference to the drawings, but the disclosure is not intended to be limited only to the embodiments described in the drawings. Further, the dimensions of the dilator illustrated in each drawing are dimensions indicated to facilitate the understanding of the contents of implementation and may not correspond to the actual dimensions. Further, an axis Z illustrated in each drawing indicates a central axis of each of a distal end section, the tapered section, and a main body section, and a central axis of the hollow shaft.

FIG. 1 is a schematic view entirely illustrating a dilator of the disclosed embodiments. As illustrated in FIG. 1, dilator 1 generally includes a hollow shaft 11, a spirally-arranged protruding portion 21, and a base section 31.

The hollow shaft 11 is a member including a tapered section 111. In the dilator 1, the hollow shaft 11 includes, in addition to the tapered section 111, a distal end section 112, a main body section 113, and a through-hole 11h.

The tapered section 111 has a diameter increasing from a distal end toward a proximal end thereof. Specifically, the tapered section 111 is connected to a distal end of the main body section 113 described later, extends from the distal end of the main body section 113 toward the distal end direction, and has a shape that tapers toward the distal end direction (a shape in which the outer diameter of the distal end is smaller than the outer diameter of the proximal end).

The distal end section 112 is a portion of which the proximal end is located at the distal end of the tapered section 111, and which extends toward the distal end direction in an axial direction of the tapered section 111. Specifically, for example, in the distal end section 112, the proximal end is continuous with the distal end of the tapered section 111 and the distal end section 112 has a substantially constant outer diameter from the distal end to the proximal end.

The main body section 113 is a portion of which the distal end is located at the proximal end of the tapered section 111 and which extends toward the proximal end direction in the axial direction of the tapered section 111. Specifically, for example, the distal end of the main body section 113 is continuous with the proximal end of the tapered section 111 described above, and the proximal end of the main body section 113 is connected to the base section 31 described later. The main body section 113 has a substantially constant outer diameter from the distal end to the proximal end thereof.

In the hollow shaft 11, it is possible to form the distal end section 112, the tapered section 111, and the main body section 113 described above integrally or separately. In the dilator 1, the distal end section 112, the tapered section 111, and the main body section 113 are formed integrally by casting or the like.

The through-hole 11h is a through-hole through which a guide wire (not illustrated), for example, or the like is inserted. The through-hole 11h includes a continuous space connecting the distal end and the proximal end of the hollow shaft 11 so that the guide wire or the like may freely pass.

The hollow shaft 11 described above is inserted into a body cavity, and thus, the hollow shaft 11 is preferably formed of a material having an antithrombotic property, flexibility, and biocompatibility, and examples of the material include a resin material such as a polyamide resin, a polyolefin resin, a polyester resin, a polyurethane resin, a silicone resin, and a fluororesin; and a metal material such as stainless steel and a superelastic alloy (a nickel-titanium alloy).

It is noted that the distal end section 112, the tapered section 111, and the main body section 113 may include various types of coatings (not illustrated) at a surface (an outer peripheral surface s11) side thereof. Examples of the coating include a protective film (a representative example of which is a plating film) for protecting the surface of the distal end section 112, the tapered section 111, and the main body section 113, and a base film for improving the adhesion between the distal end section 112, the tapered section 111, and the main body section 113, and the spirally-arranged protruding portion 21 described later.

The spirally-arranged protruding portion 21 are provided on the outer peripheral surface s11 of the hollow shaft 11 and include gaps 213 between neighboring sections of the spirally-arranged protruding portion 21 along the axial direction of the hollow shaft 11. Specifically, for example, the spirally-arranged protruding portion 21 protrudes from the outer peripheral surface s11 of the shaft 11 outward in a radial direction of the hollow shaft 11, and the neighboring protrusion sections 21 are arranged to be distant from each other in the axial direction (to include the gap 213).

Here, as illustrated in FIG. 2, the spirally-arranged protruding portion 21 includes an apex section 211 having the greatest height from the outer peripheral surface s11 in a transverse cross-section of the protrusion section 21, and a side surface section 212 facing outward and extending from the apex section 211 toward the outer peripheral surface s11.

Further, in the spirally-arranged protruding portion 21, the side surface section 212 includes an inclined surface 212a that is inclined substantially linearly toward the distal end direction and/or the proximal end direction between the outer peripheral surface s11 and the apex section 211 in a transverse cross-section of the spirally-arranged protruding portion 21 (a substantially planar inclined surface that faces outward in a radial direction of the Z-axis and is inclined monotonically with respect to the Z-axis, that is, an inclined surface formed so that a distance between any point on the inclined surface and the Z-axis gradually decreases toward the distal end direction or the proximal end direction). The inclined surface 212a may be formed at any portion of the side surface section 212 and may include, for example, an inclined surface that is formed from the distal end or the proximal end of the apex section to the outer peripheral surface s11, an inclined surface that is formed from the distal end or the proximal end of the apex section to somewhere along the side surface section, and an inclined surface that is formed from somewhere along the side surface section to the outer peripheral surface s11. In the dilator 1, the spirally-arranged protruding portion 21 includes an inclined surface 212a1 having a planar shape, in the side surface section 212 facing the distal end direction, and the inclined surface 212a1 is formed from the distal end of the apex section 211 to somewhere along the side surface section 212.

The spirally-arranged protruding portion 21 may be formed as a continuous or discontinuous single-thread or multi-thread projection in the axial direction. Further, the spirally-arranged protruding portion 21 may be formed integrally with or separately from the hollow shaft 11. In the dilator 1, the spirally-arranged protruding portion 21 is formed as a continuous, single-thread projection, and is formed integrally with the hollow shaft 11 by casting or the like.

Here, it is preferable that the spirally-arranged protruding portion 21 does not form a cutting edge (does not have a shape that cuts a living tissue). That is, it is preferable that, in a shape of a transverse cross-section of the spirally-arranged protruding portion 21 (a cross-section orthogonal to a helical direction of the spirally-arranged protruding portion 21), an outer end section of the shaft 11 in the radial direction (the apex section 211) does not have an acute-angled corner section. Examples of such an end section include an end section formed of an obtuse-angled corner section, and an end section formed of a corner section having a shape including a curve (such as a curve including a part of a circle or an ellipse). This shape enables the dilator 1 to dilate a hole of a target object without damaging a living tissue on an inner surface of the hole.

A material for forming the spirally-arranged protruding portion 21 is not particularly limited as long as an effect of the disclosed embodiments is not impaired, and examples thereof may include a metallic material such as stainless steel and a superelastic alloy (a nickel-titanium alloy); and a resin material having biocompatibility such as a polyamide resin and a fluororesin.

The base section 31 is a portion where an operator operates the dilator 1. A distal end of the base section 31 is connected to a proximal end of the main body section 113 in the hollow shaft 11, and the hole is dilated by rotating the hollow shaft 11 or linearly pushing the hollow shaft 11 by operating the base section 31. The base section 31 includes a through-hole 31h communicating with the through-hole 11h of the shaft 11 (see FIG. 1), and a guide wire or the like is inserted into the through-hole 31h.

As for a length in the axial direction in each section of the dilator 1, a whole of the shaft 11 may be from 1600 mm to 2500 mm, the distal end section 112 may be from 0 mm to 100 mm, and the tapered section 111 may be from 5 mm to 100 mm. As for an outer diameter in each section of the shaft 11, distal ends of the distal end section 112 and the tapered section 111 may be from 0.8 mm to 3.0 mm, and a proximal end of the tapered section 111 and the main body section 113 may be from 1.4 mm to 5.0 mm. An inner diameter of the through-hole 11h of the shaft 11 may be from 0.4 mm to 1.0 mm. The height of the spirally-arranged protruding portion 21 may be from 0.125 mm to 0.5 mm.

As for a length in the axial direction in each section of the dilator 1, a whole of the shaft 11 is 2000 mm, the distal end section 112 is 10 mm, and the tapered section 111 is 30 mm. As for an outer diameter of each section of the shaft 11, distal ends of the distal end section 112 and the tapered section 111 are 1.84 mm, and a proximal end of the tapered section 111 and the main body section 113 are 2.64 mm. An inner diameter of the through-hole 11h of the shaft 11 is 0.7 mm. The height of the spirally-arranged protruding portion 21 is 0.3 mm.

Next, an example of a usage mode of the dilator 1 will be described.

Firstly, a target object is punctured with an introducer needle (not illustrated) to form a hole. Next, after a guide wire (not illustrated) is inserted into a lumen of the introducer needle, the introducer needle is pulled out.

Next, the proximal end of the guide wire is inserted into the through-hole 11h of the dilator 1, and the dilator 1 is pushed forward to a location of the hole in the target object (hereinafter, also referred to as a "punctured section"), to insert the distal end section 112 and the tapered section 111 in this order into the hole. Next, the base section 31 is operated to rotate the hollow shaft 11 or to linearly push the hollow shaft 11, so that the hollow shaft 11 is advanced to pass the tapered section 111 into the punctured section to dilate the hole.

As described above, in the dilator 1, the side surface section 212 includes the inclined surface 212a that is inclined substantially linearly toward the distal end direction between the outer peripheral surface s11 and the apex section 211 in the transverse cross-section of the spirally-arranged protruding portion 21, and thus, in addition to advancing the dilator 1 by a screwing action (generation of a propulsive force) of the spirally-arranged protruding portion 21 resulting from the rotation of the hollow shaft 11, it is also possible to smoothly push the dilator 1 linearly, and a combination of these operations enables the hole to be dilated efficiently. It is presumed that this effect can be obtained because, when the hollow shaft 11 is advanced, the resistance between the hollow shaft 11 and a contact object is reduced by the configuration described above.

It is noted that, in the dilator, it is only required that the inclined surface 212a described above is provided in at least any one of a side surface section facing the distal end direction and a side surface section facing the proximal end direction in the spirally-arranged protruding portion, and examples of the dilator include a dilator 1m1 including an inclined surface 212am1 on a whole of a side surface section 212m1 facing the distal end direction (see FIG. 3A), a dilator 1m2 including an inclined surface 212am2 on a part of a side surface section 212m2 facing the proximal end direction (see FIG. 3B), a dilator 1m3 including an inclined surface 212am3 on a whole of a side surface section 212m3 facing the proximal end direction (see FIG. 3C), a dilator 1m4 including inclined surfaces 212am41 and 212am42 on a part of side surface sections 212m41 and 212m42 facing the distal end direction and the proximal end direction, respectively (see FIG. 3D), and a dilator 1m5 including inclined surfaces 212am51 and 212am52 on a whole of side surface sections 212m51 and 212m52 facing the distal end direction and the proximal end direction, respectively (see FIG. 3E).

The dilators 1m2 to 1m5 having inclined surfaces facing the proximal end direction can retreat the dilators 1m2 to 1m5 by a screwing action (generation of a propulsive force) of the spirally-arranged protruding portion 21 resulting from a reverse rotation of the hollow shaft 11 and also smoothly be pulled out linearly. Further, according to the dilators 1m4 and 1m5 having inclined surfaces facing the distal end direction and the proximal end direction, when the dilators 1m4 and 1m5 are pushed into the target object, the dilators 1m4 and 1m5 can be advanced by a screwing action (generation of a propulsive force) of the spirally-arranged protruding portion 21 resulting from the rotation of the hollow shaft 11, and also smoothly be pushed therein linearly. When the dilators 1m4 and 1m5 are pulled out, the dilators 1m4 and 1m5 can be retreated by a screwing action (generation of a propulsive force) of the spirally-arranged protruding portion 21 resulting from a reverse rotation of the hollow shaft 11, and also smoothly be pulled out linearly.

FIG. 4 is an enlarged schematic end view illustrating a spirally-arranged protruding portion of a dilator of the disclosed embodiments. As illustrated in FIG. 4, dilator 2 generally includes the hollow shaft 11, a spirally-arranged protruding portion 22, and the base section 31 (not illustrated). The dilator 2 is different from that in the dilator 1 in that the dilator 2 includes the spirally-arranged protruding portion 22. It is noted that portions identical to those in the dilator 1 are designated by the same reference numerals, and description thereof will not be repeated. Further, the spirally-arranged protruding portion 22 is configured in the same way, except for a shape, as the spirally-arranged protruding portion 21 in the dilator 1, and thus, description thereof will not be repeated.

The spirally-arranged protruding portion 22 are provided on the outer peripheral surface s11 of the hollow shaft 11 and include gaps 223 between neighboring sections of the spirally-arranged protruding portion 22 along the axial direction of the hollow shaft 11. The spirally-arranged protruding portion 22 includes an apex section 221 having the greatest height from the outer peripheral surface s11 in a transverse cross-section of the spirally-arranged protruding portion 22, and a side surface section 222 facing outward and extending from the apex section 221 toward the outer peripheral surface s11, and the side surface section 222 includes an inclined surface 222a that is inclined substantially linearly toward the distal end direction and/or the proximal end direction between the outer peripheral surface s11 and the apex section 221 in a transverse cross-section of the spirally-arranged protruding portion 22.

In the spirally-arranged protruding portion 22 of the dilator 2, a contour line of the side surface section 222 in a transverse cross-section of the spirally-arranged protruding portion 22 includes a concave-shaped portion (hereinafter, simply referred to as a "concave section") 222b. Specifically, as illustrated in FIG. 4, the spirally-arranged protruding portion 22 can be configured to include a concave section 222b1 having a curved shape in a part of the side surface section 222 facing the distal end direction, for example.

As described above, the dilator 2 includes the portion 222b1 in which the contour line of the side surface section 222 has a concave shape in the transverse cross-section of the spirally-arranged protruding portion 22, and thus, the rigidity of the spirally-arranged protruding portion 22 can be reduced, and as a result, it is possible to improve the flexibility of the dilator 2.

In the dilator 2, it is only required that the contour line of the side surface section 222 described above includes the concave section 222b, and examples of such dilator include a dilator 2m1 including a concave section 222bm1 having a curved shape in a part of a side surface section 222m1 facing the distal end direction (see FIG. 5A), a dilator 2m2 including a concave section 222bm2 having a polygonal shape (a shape combining two or more planar surfaces) on a whole of a side surface section 222m2 facing the distal end direction (see FIG. 5B), and a dilator 2m3 including concave sections 222bm31 and 222bm32 having a curved shape and a polygonal shape in side surface sections 222m31 and 222m32 facing the distal end direction and the proximal end direction, respectively (see FIG. 5C).

FIG. 6 is a schematic side view entirely illustrating a dilator of the disclosed embodiments. As illustrated in FIG. 6, dilator 3 generally includes a hollow shaft 13, a spirally-arranged protruding portion 23, and the base section 31. The dilator 3 is different from that in the dilator 1 in that the dilator 3 includes the hollow shaft 13 and the spirally-arranged protruding portion 23. It is noted that portions identical to those in the dilator 1 are designated by the same reference numerals, and description thereof will not be repeated. Further, the hollow shaft 13 and the spirally-arranged protruding portion 23 are configured in the same way, except for a shape, as the hollow shaft 11 and the spirally-arranged protruding portion 21 in the dilator 1, respectively, and thus, description thereof will not be repeated.

The hollow shaft 13 is a member including a tapered section 131. The hollow shaft 13 includes, in addition to the tapered section 131, a distal end section 132, a main body section 133, and a through-hole 13h. The tapered section 131 is a portion of which the outer diameter at the distal end is smaller than the outer diameter at the proximal end. The distal end section 132 is a portion of which the proximal end is located at the distal end of the tapered section 131, and which extends toward the distal end direction in an axial direction of the tapered section 131. The main body section 133 is a portion of which the distal end is located at the proximal end of the tapered section 131 and which extends toward the proximal end direction in the axial direction of the tapered section 131. The through-hole 13h is a through-hole through which a guide wire (not illustrated) or the like is inserted, for example.

The hollow shaft 13 of the present embodiment is formed of a coil body 13c (hereinafter, also referred to as a "first coil body 13c") formed by winding a wire around an axis of the hollow shaft 13. The first coil body 13c may be formed, for example, by using one strand or a plurality of strands of wire to wind the wire so that neighboring strands of the wire are in close contact with each other along the axial direction of the hollow shaft 13. It is noted that the distal end section 132, the tapered section 131, and the main body section 133 of the hollow shaft 13 mentioned above are defined in accordance with a shape of an outer peripheral surface s13 of the first coil body 13c. Further, a space formed inside the first coil body 13c (a region inside a broken line in FIG. 6) is the through-hole 13h.

FIG. 7 is an enlarged schematic end view illustrating the spirally-arranged protruding portion 23 of a dilator of the disclosed embodiments. The spirally-arranged protruding portion 23 is provided on the outer peripheral surface s13 of the hollow shaft 13 and includes gaps 233 between neighboring sections of the spirally-arranged protruding portion 23 along the axial direction of the hollow shaft 13. As illustrated in FIG. 7, the spirally-arranged protruding portion 23 includes an apex section 231 having the greatest height from the outer peripheral surface s13 in a transverse cross-section of the spirally-arranged protruding portion 23, and a side surface section 232 facing outward and extending from the apex section 231 toward the outer peripheral surface s13. Further, in the spirally-arranged protruding portion 23, the side surface section 232 includes an inclined surface 232a that is inclined substantially linearly toward the distal end direction and/or the proximal end direction between the outer peripheral surface s13 and the apex section 231 in the transverse cross-section of the spirally-arranged protruding portion 23.

As illustrated in FIG. 7, the spirally-arranged protruding portion 23 is formed of a coil body 23c (hereinafter, also referred to as a "second coil body 23c") formed by winding a wire around the outer peripheral surface s13 of the hollow shaft 13. Specifically, the second coil body 23c is formed to include the inclined surface 232a in a part of the side surface section 232 facing the distal end direction, for example, and the second coil body 23c may be configured so that the side surface section 232 includes an inclined surface 232a1 that is inclined substantially linearly toward the distal end direction between the outer peripheral surface s13 and the apex section 231 in a transverse cross-section of the spirally-arranged protruding portion 23. The second coil body 23c described above may be formed as a single-thread or multi-thread coil body by using, for example, one strand or a plurality of strands of wire.

Here, the diameter of the wire forming the first coil body 13c may be from 0.1 mm to 0.5 mm, and the diameter of the wire forming the second coil body 23c may be from 0.1 mm to 0.5 mm. In an example of the present embodiment, the diameter of the wire of the first coil body 13c is 0.21 mm, and the diameter of the wire of the second coil body 23c is 0.36 mm.

Examples of a material of the wire forming the first coil body 13c and the second coil body 23c include a material forming the distal end section 112, the tapered section 111, and the main body section 113 described in the dilator 1, and a material similar to the one exemplified as the material forming the spirally-arranged protruding portion 21.

Here, the first coil body 13c and the second coil body 23c may be joined, for example, at a joint part located at end sections of the second coil body 23c in the distal end direction and the proximal end direction (a portion where the second coil body 23c and the hollow shaft 13 are joined, not illustrated). A method of joining the first coil body 13c and the second coil body 23c may employ, for example, a method of directly joining the first coil body 13c and the second coil body 23c and a method of indirectly joining the first coil body 13c and the second coil body 23c.

Examples of the method of directly joining the first coil body 13c and the second coil body 23c mentioned above include a thermal welding method using laser light such as a YAG laser (laser welding method), and a method of utilizing a contact resistance or the like of an interface where the first coil body 13c and the second coil body 23c contact each other, to weld the first coil body 13c and the second coil body 23c by passing an electric current (resistance welding method). On the other hand, examples of the method of indirectly joining the first coil body 13c and the second coil body 23c mentioned above include a method of brazing the first coil body 13c and the second coil body 23c with, for example, a metal brazing filler formed of a Sn—Pb alloy, Pb—Ag alloy, Sn—Ag alloy, and Au—Sn alloy (brazing method), a method of bonding the first coil body 13c and the second coil body 23c with an adhesive, and a method of welding the first coil body 13c and the second coil body 23c with a coating.

Among these methods, the method of directly joining the first coil body 13c and the second coil body 23c is preferable for the above-mentioned joining method because this eliminates another member such as a brazing filler material, and the laser welding method is more preferable because this eliminates application of pressure to prevent an undesirable deformation. In the dilator 3, the first coil body 13c and the second coil body 23c are joined at a predetermined joint part by the laser welding method.

As described above, in the dilator 3, the spirally-arranged protruding portion 23 is formed of the second coil body 23c, and thus, it is possible to improve the flexibility and the torquability of the spirally-arranged protruding portion 23. Further, in the dilator 3, in addition to the second coil body 23c, the hollow shaft 13 is formed of the first coil body 13c, and thus, it is possible to further improve the flexibility and the torquability by the combination of the first and second coil bodies 13c and 23c.

In the dilator 3, it is only required that the inclined surface 232a described above is provided in at least any one of a side surface section facing the distal end direction and a side surface section facing the proximal end direction in the spirally-arranged protruding portion 23, and examples of the dilator 3 include a dilator 3m1 including an inclined surface 232am1 on a whole of a side surface section 232m1 facing the distal end direction (see FIG. 8A), a dilator 3m2 including an inclined surface 232am2 on a part of a side surface section 232m2 facing the proximal end direction (see FIG. 8B), a dilator 3m3 including an inclined surface 232am3 on a whole of a side surface section 232m3 facing the proximal end direction (see FIG. 8C), a dilator 3m4 including inclined surfaces 232am41 and 232am42 on a part of side surface sections 232m41 and 232m42 facing the distal end direction and the proximal end direction, respectively (see FIG. 8D), and a dilator 3m5 including inclined surfaces 232am51 and 232am52 on a whole of side surface sections 232m51 and 232m52 facing the distal end direction and the proximal end direction, respectively (see FIG. 8E). According to a dilator having an inclined surface facing the distal end direction and/or the proximal end direction, an effect similar to the effect described in the dilator 1 can be exhibited.

FIG. 9 is an enlarged schematic end view illustrating a spirally-arranged protruding portion of a dilator of the disclosed embodiments. As illustrated in FIG. 9, dilator 4 generally includes the hollow shaft 13, a joint part 44, a spirally-arranged protruding portion 24, and the base section 31 (not illustrated). The dilator 4 is different from the dilator 3 in that the dilator 4 includes the joint part 44 and the spirally-arranged protruding portion 24. Portions identical to those in the dilator 3 are designated by the same reference numerals, and description thereof will not be repeated.

The spirally-arranged protruding portion 24 are provided on the outer peripheral surface s13 of the first coil body 13c (the hollow shaft 13) and include gaps 243 between neighboring sections of the spirally-arranged protruding portion 24 along the axial direction of the first coil body 13c. The spirally-arranged protruding portion 24 includes an apex section 241 having the greatest height from the outer peripheral surface s13 in a transverse cross-section of the spirally-arranged protruding portion 24, and a side surface section 242 facing outward and extending from the apex section 241 toward the outer peripheral surface s13, and the side surface section 242 includes an inclined surface 242a that is inclined substantially linearly toward the distal end direction and/or the proximal end direction between the outer peripheral surface s13 and the apex section 241 in a transverse cross-section of the spirally-arranged protruding portion 24.

As illustrated in FIG. 9, the spirally-arranged protruding portion 24 of the dilator 4 includes an inclined surface 242a1 in the side surface section 242 facing the distal end direction, and the inclined surface 242a1 is arranged in a portion of a second coil body 24c directly above the joint part 44 (a portion where the first coil body 13c and the second coil body 24c are joined). It is only required that at least a part of the inclined surface 242a1 is arranged in a portion of the spirally-arranged protruding portion directly above the joint part 44, and a portion of the spirally-arranged protruding portion 24 other than the portion directly above the joint part 44 may also include an inclined surface.

A method of forming the joint part 44 may employ, for example, a method similar to the method of joining the first coil body 13c and the second coil body 23c described in the dilator 3. In the dilator 4, the first coil body 13c and the second coil body 24c are joined at a joint part by the laser welding method.

As described above, in the dilator 4, the inclined surface 242a1 is arranged in a portion of the second coil body 24c directly above the joint part 44, so that the resistance between the spirally-arranged protruding portion 24 above the joint part 44 and a contact object (not illustrated) can be reduced, and the second coil body 24c can be prevented from leaving the first coil body 13c (the hollow shaft 13).

Fifth Embodiment

FIG. 10 is an enlarged schematic end view illustrating a spirally-arranged protruding portion of a dilator of the disclosed embodiments. As illustrated in FIG. 10, dilator 5 generally includes the hollow shaft 13, a spirally-arranged protruding portion 25, and the base section 31 (not illustrated). The dilator 5 is different from that in the dilator 3 in that the dilator 5 includes the spirally-arranged protruding portion 25. Portions identical to those in the dilator 3 are designated by the same reference numerals, and description thereof will not be repeated.

The spirally-arranged protruding portion 25 are provided on the outer peripheral surface s13 of the first coil body 13c (the hollow shaft 13) and includes gaps 253 between neighboring sections of the spirally-arranged protruding portion 25 along the axial direction of the first coil body 13c. Each of the spirally-arranged protruding portion 25 includes an apex section 251 having the greatest height from the outer peripheral surface s13 in a transverse cross-section of the spirally-arranged protruding portion 25, and a side surface section 252 facing outward and extending from the apex section 251 toward the outer peripheral surface s13, and the side surface section 252 includes an inclined surface 252a that is inclined substantially linearly toward the distal end direction and/or the proximal end direction between the outer peripheral surface s13 and the apex section 251 in a transverse cross-section of the spirally-arranged protruding portion 25.

The spirally-arranged protruding portion 25 is formed of a coil body 25c (hereinafter, also referred to as a "second coil body 25c") formed by winding a wire around the outer peripheral surface s13 of the first coil body 13c. The second coil body 25c may be configured to include, for example, in the side surface section 252 facing the distal end direction, the inclined surface 252a mentioned above, and a portion (concave section) 252b in which a contour line of the side surface section 252 has a concave shape in a transverse cross-section of the spirally-arranged protruding portion 25. In the dilator 5, an example is described in which the concave section 252b is a concave section 252b1 having a curved shape.

As described above, the dilator 5 includes the portion 252b1 in which the contour line of the side surface section 252 has a concave shape in the transverse cross-section of the spirally-arranged protruding portion 25, and thus, the rigidity of the spirally-arranged protruding portion 25 can be reduced, and further, the spirally-arranged protruding portion 25 is formed of the second coil body 25c, and therefore, the flexibility of the dilator 5 can be further improved by the combination of the concave section 252b and the second coil body 25c.

In the dilator 5, it is only required that the contour line of the side surface section 252 described above includes the concave section 252b, and examples of the dilator 5 include a dilator 5m1 including a concave section 252bm1 having a curved shape in a part of a side surface section 252m1 facing the distal end direction (see FIG. 11A), a dilator 5m2 including a concave section 252bm2 having a curved shape in a part of a side surface section 252m2 facing the proximal end direction (see FIG. 11B), a dilator 5m3 including a concave section 252bm3 having a polygonal shape (a shape combining two or more planar surfaces) on a whole of a side surface section 252m3 facing the proximal end direction (see FIG. 11C), and a dilator 5m4 including concave sections 252bm41 and 252bm42 having a curved shape and a polygonal shape in side surface sections 252m41 and 252m42 facing the distal end direction and the proximal end direction, respectively (see FIG. 11D).

The disclosed embodiments are not limited to the configuration of the above-described embodiments, but is indicated by the claims, and is intended to include all modifications within meanings and the scope equivalent to the claims.

For example, in the above-described embodiment, description is given of the dilators 1 to 5 in which the spirally-arranged protruding portion 21 to 25 including the inclined surfaces 212a, 222a, 232a, 242a, and 252a are each provided in the distal end section of the hollow shafts 11 and 13. However, in the dilators, it is only required that the spirally-arranged protruding portion is provided on an outer peripheral surface of at least any one of the distal end section, the tapered section, and the main body section of the hollow shaft, and examples of the dilator may include, even though not illustrated here, a dilator in which the spirally-arranged protruding portion including the inclined surface mentioned above is provided on a whole of the distal end section, the tapered section, and the main body section, and a dilator in which the spirally-arranged protruding portion including the inclined surface mentioned above is only provided in the tapered section and the main body section. Further, the dilator may be a dilator in which a spirally-arranged protruding portion including an inclined surface and a spirally-arranged protruding portion not including an inclined surface are both provided in each of the distal end section, the tapered section, and the main body section.

Further, in the embodiments described above, description is given of the dilators 1 to 5 in which the hollow shafts 11 and 13 include the distal end sections 112 and 132, the tapered sections 111 and 131, and the main body sections 113 and 133. However, it is only required that the dilators include a tapered section in which a diameter of the hollow shaft increases from the distal end to the proximal end, and the dilator may include, for example, a dilator provided with a hollow shaft including the tapered section and the main body section, but not including the distal end section. Examples of such a dilator include a dilator 6*m*1 in which a hollow shaft 16*m*1 and a spirally-arranged protruding portion 26*m*1 are integrally formed (see FIG. 12), and a dilator 6*m*2 in which a hollow shaft 16*m*2 and a spirally-arranged protruding portion 26*m*2 are each formed of a coil body (see FIG. 13).

Further, in the dilator 1 described above, description is given of the dilator in which the hollow shaft 11 and the spirally-arranged protruding portion 21 are integrally formed, and in the dilator 3, description is given of the dilator in which the hollow shaft 13 and the spirally-arranged protruding portion 23 are formed of the coil bodies 13*c* and 23*c*. However, the dilator may be, for example, a dilator 6*m*3 in which a shaft 16*m*3 including a distal end section, a tapered section, and a main body section is formed integrally and a spirally-arranged protruding portion 26*m*3 is formed of a second coil body (see FIG. 14), a dilator 6*m*4 in which a shaft 16*m*4 including a tapered section and a main body section is formed integrally and a spirally-arranged protruding portion 26*m*4 is formed of a second coil body (see FIG. 15), and the like.

Further, in the dilator 1 described above, description is given of the dilator in which the spirally-arranged protruding portion 21 is formed on the outer peripheral surface s11 of the hollow shaft 11 from the distal end to somewhere along the axial direction. However, the dilator may be a dilator in which a spirally-arranged protruding portion is formed on the entire outer peripheral surface of the shaft in the axial direction.

Further, in the dilator 3 described above, description is given of the dilator in which the spirally-arranged protruding portion 23 (the second coil body 23*c*) includes the gaps 233 between neighboring sections of the spirally-arranged protruding portion 23 from the distal end to somewhere along the axial direction on the outer peripheral surface s13 of the hollow shaft 13, and the neighboring sections contact each other from the point partway to the proximal end. However, the dilator may be a dilator in which the spirally-arranged protruding portion (the second coil body) includes gaps between neighboring sections on the entire outer peripheral surface of the shaft in the axial direction (from the distal end to the proximal end).

The invention claimed is:

1. A dilator comprising:
   a hollow shaft comprising a tapered section having a diameter increasing from a distal end toward a proximal end of the hollow shaft; and
   a spirally-arranged protruding portion provided on an outer peripheral surface of the hollow shaft, the spirally-arranged protruding portion comprising (i) spirally-arranged protruding sections, and (ii) gaps between adjacent spirally-arranged protruding sections along an axial direction of the hollow shaft,
   wherein the spirally-arranged protruding portion includes:
      (i) an apex section having a greatest height from the outer peripheral surface in a transverse cross-section of the spirally-arranged protruding portion, and
      (ii) a side surface section facing outward and extending from the apex section toward the outer peripheral surface, the side surface section including an inclined surface inclined substantially linearly toward at least one of a distal end direction and a proximal end direction between the outer peripheral surface and the apex section in the transverse cross-section of the spirally-arranged protruding portion, and
   the spirally-arranged protruding portion comprises a coil body formed by winding a wire around the outer peripheral surface of the hollow shaft.

2. The dilator according to claim 1, wherein a contour line of the side surface section in the transverse cross-section of the spirally-arranged protruding portion includes a portion having a concave shape.

3. The dilator according to claim 1, wherein the coil body and the hollow shaft are joined at a joint, and
   at least a part of the inclined surface is arranged in a portion of the coil body directly above joint.

* * * * *